US010667928B2

(12) United States Patent
Goldstein

(10) Patent No.: US 10,667,928 B2
(45) Date of Patent: Jun. 2, 2020

(54) PROSTHETIC LIMB AND PROSTHETIC LIMB ATTACHMENT FOR SWIMMING

(71) Applicant: The Feinstein Institute for Medical Research, Manhasset, NY (US)

(72) Inventor: Todd Goldstein, Manhasset, NY (US)

(73) Assignee: THE FEINSTEIN INSTITUTES FOR MEDICAL RESEARCH, Manhasset, NY (US)

(*) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 15/969,194

(22) Filed: May 2, 2018

(65) Prior Publication Data

US 2018/0318111 A1    Nov. 8, 2018

Related U.S. Application Data

(60) Provisional application No. 62/500,316, filed on May 2, 2017.

(51) Int. Cl.
*A61F 2/60*    (2006.01)
*A61F 2/66*    (2006.01)
*A61F 2/80*    (2006.01)
*A61F 2/50*    (2006.01)

(52) U.S. Cl.
CPC ............... *A61F 2/66* (2013.01); *A61F 2/60* (2013.01); *A61F 2/80* (2013.01); *A61F 2002/5081* (2013.01); *A61F 2002/5083* (2013.01); *A61F 2002/5089* (2013.01); *A61F 2002/607* (2013.01); *A61F 2002/6614* (2013.01)

(58) Field of Classification Search
CPC ............ A61F 2/601; A61F 2002/607; A61F 2002/5089; A61F 2/60; A63B 31/12
See application file for complete search history.

(56) References Cited

U.S. PATENT DOCUMENTS

| 4,822,363 | A | * | 4/1989 | Phillips | A61F 2/60 623/27 |
| 5,156,630 | A | * | 10/1992 | Rappoport | A61F 2/6607 403/103 |
| 7,285,030 | B1 | * | 10/2007 | Houck | A63B 31/12 441/60 |
| 2018/0318111 | A1 | * | 11/2018 | Goldstein | A61F 2/66 |

OTHER PUBLICATIONS

Bruce Brown, Apr. 19, 2017, Prosthetic Leg with Fin Helps Amputees Swim, HealthTech Insider.*

* cited by examiner

*Primary Examiner* — Bruce E Snow
(74) *Attorney, Agent, or Firm* — Amster, Rothstein & Ebenstein LLP

(57) ABSTRACT

A prosthesis including a socket configured to receive a residual limb, a pylon attached to the socket, the pylon comprising at least one fin, and an artificial foot attached to an end portion of the pylon.

7 Claims, 2 Drawing Sheets

PROSTHETIC LIMB AND PROSTHETIC LIMB ATTACHMENT FOR SWIMMING

RELATED APPLICATION

This application is a non-provisional claiming priority to and the benefit of U.S. Provisional Application 62/500,316, filed May 2, 2017 and entitled PROSTHETIC LIMB AND PROSTHETIC LIMB ATTACHMENT FOR SWIMMING, the contents of which are incorporated herein by reference in their entirety.

FIELD OF THE INVENTION

The present invention relates to prosthetic limbs, and in particular to prosthetic limbs intended for use in water.

BACKGROUND OF THE INVENTION

A limb prosthesis is ideally designed to replace the full functionality and mobility originally provided by the wearer's lost native limb. The goal is to allow the wearer to return to his/her original lifestyle and activities without undue physical hardship or concern for damage to the prosthetic. In this regard, a particular issue exists with conventional prosthetics in that such prosthetics do not allow for "amphibious" use. That is, in order for a wearer to enter and perform activities in the water, such as a pool or ocean, the wearer must remove the prosthetic intended for everyday use and replace it with one more suitable for use in water. For example, conventional transtibial prosthetics exist that include a fin in place of a foot, which allows the prosthetic to function effectively in water, but renders the prosthetic mostly inoperable for use on land.

SUMMARY OF THE INVENTION

An object of this invention is to provide a prosthesis that has amphibious functionality. That is, the prosthesis according to exemplary embodiments of the present invention is suitable for use on both land and in a water environment, such as a pool or ocean.

Another object of this invention is to provide a prosthesis and prosthesis attachment that allows a wearer to perform everyday activities in a land environment, enter a water environment, such as a pool or ocean, perform activities in the water environment and then return to the land environment without requiring removal or replacement of the prosthesis.

Accordingly, an exemplary embodiment of the present invention for use as an amphibious lower leg prosthetic in the instance of a below-the-knee amputation comprises: a socket configured to receive a residual limb; a pylon proximally attached to the socket, the pylon comprising at least one fin; and an artificial foot attached to a distal end portion of the pylon.

In at least one exemplary embodiment, the at least one fin comprises two fin members, each of the fin members angled inwardly along the length of the pylon from the socket to the artificial foot.

In at least one exemplary embodiment, each fin member comprises at least one hole.

In at least one exemplary embodiment, each fin member comprises a plurality of holes positioned along the length of the fin member.

In at least one exemplary embodiment, the at least one fin is reversibly detachable from, and re-attachable to, the pylon.

In at least one exemplary embodiment, the at least one fin and the pylon are a unitary structure.

BRIEF DESCRIPTION OF THE DRAWINGS

The above and related objects, features and advantages of the present invention will be more fully understood by reference to the following, detailed description of the preferred, albeit illustrative, embodiments of the present invention when taken in conjunction with the accompanying figures, wherein.

DETAILED DESCRIPTION OF THE INVENTION

Figure 1:
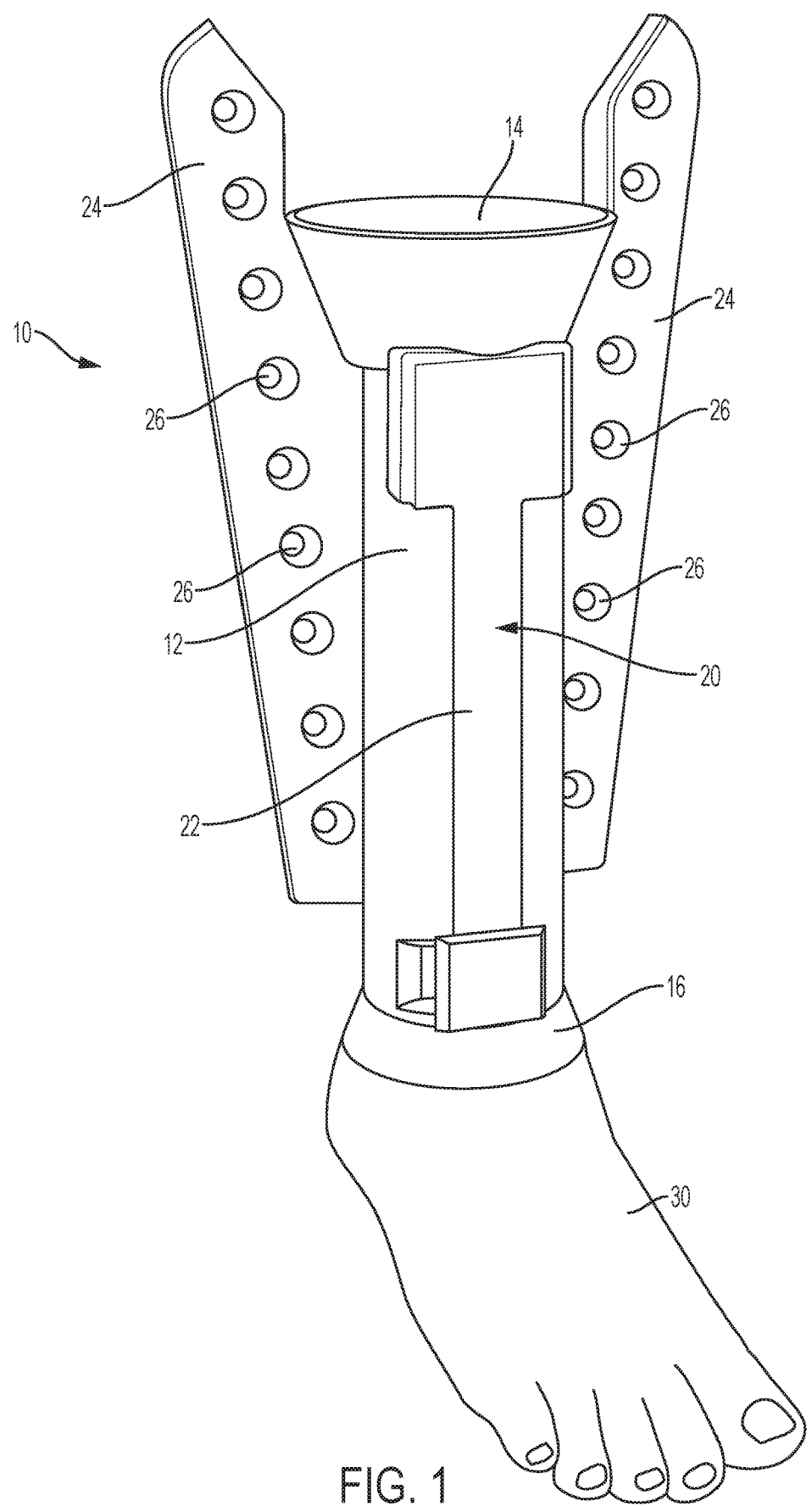
FIG. 1 is a perspective view of prosthesis according to an exemplary embodiment of the present invention.

FIG. 1 shows a perspective view of a transtibial prosthesis, generally designated by reference number 10, according to an exemplary embodiment of the present invention. The prosthesis 10 includes a pylon 12 having a generally cylindrical shape intended to replace the load-bearing function of the wearer's amputated tibia and other lower leg anatomy. The pylon 12 may be adjustable in length to obtain the proper height of the prosthesis 10. A socket 14 extends from an upper (proximal) end portion of the pylon 12 and allows for attachment of the residual limb to the prosthetic 10. As known in the art, the socket 14 may be attached to the pylon 12 by a socket adaptor and may contain liners to act as padding and provide suspension. An ankle 16 extends from a lower (distal) end portion of the pylon 12 and allows for attachment of a prosthetic foot 30. The ankle 16 may be fixedly attached to the prosthetic foot 30 or a hinge mechanism may be included between the ankle 16 and prosthetic foot 30 to allow the prosthetic foot 30 to flex relative to the prosthesis 10. Although not shown, the prosthesis 10 may include an endoskeletal finish that covers all or portions of the prosthesis 10 and protects the internal components from moisture, dust and dirt.

According to an exemplary embodiment, the prosthesis 10 includes a swim attachment, generally designated by reference number 20, that is affixed to the pylon 10. The swim attachment 20 includes a base member 22 that is formed integrally with the pylon 10 or is releasably attached to the pylon 10 by interference fit (e.g., a flexible snap-on attachment) or by any suitable mechanism, such as, for example, a buckle, tie, or fastener. In this regard, the swim attachment 20 may be slid in position over the pylon 10. Whether releasably attached or permanently affixed to the pylon 10, the swim attachment 20 does not interfere with the wearer's ability to walk on land, while enhancing the wearer's mobility within water. Specifically, the swim attachment 20 further includes fin members 24, with one fin member 24 extending longitudinally along one side of the pylon 10 and a second fin member 24 extending longitudinally along another side of the pylon 10. Each fin member 24 is tapered inwardly along the length of the fin member 24 from the socket 14 to the artificial foot. The fin members 24 include one or a series of openings or holes 26 positioned along their length. The number and/or size of the holes 26 may be determined to adjust water resistance of the fins 24, and in particular may be adjusted so that the water resistance of the prosthesis 10, including the fins 24, matches or is substantially the same as the water resistance of the wearer's intact leg. In this regard, the drag force generated by the prosthesis 10 may be calculated as follows:

$$F_{drag} = \tfrac{1}{2}(\rho A C_d v^2), \quad (1)$$

where, $C_d$—is the drag coefficient;

$\rho$—is the mass density of the fluid (equal to 1 g/cm$^3$ for water);

v—is the flow speed of the object relative to the fluid; and

A—is the reference area.

For example, for a fin with holes having a surface area of 0.1255 m$^2$, and assuming Cd=0.8, v=5 m/s, and $\rho$=1 g/cm$^3$, the drag force generated by the fin may be calculated using equation (1) to be 1.255 Newtons. This value may be compared to the drag force value of the intact leg so that appropriate adjustments may be made to the fin to achieve a more balanced propulsion through the water. For example, the area of the fin, the position of the holes and/or the number of holes may be adjusted.

Figure 2:
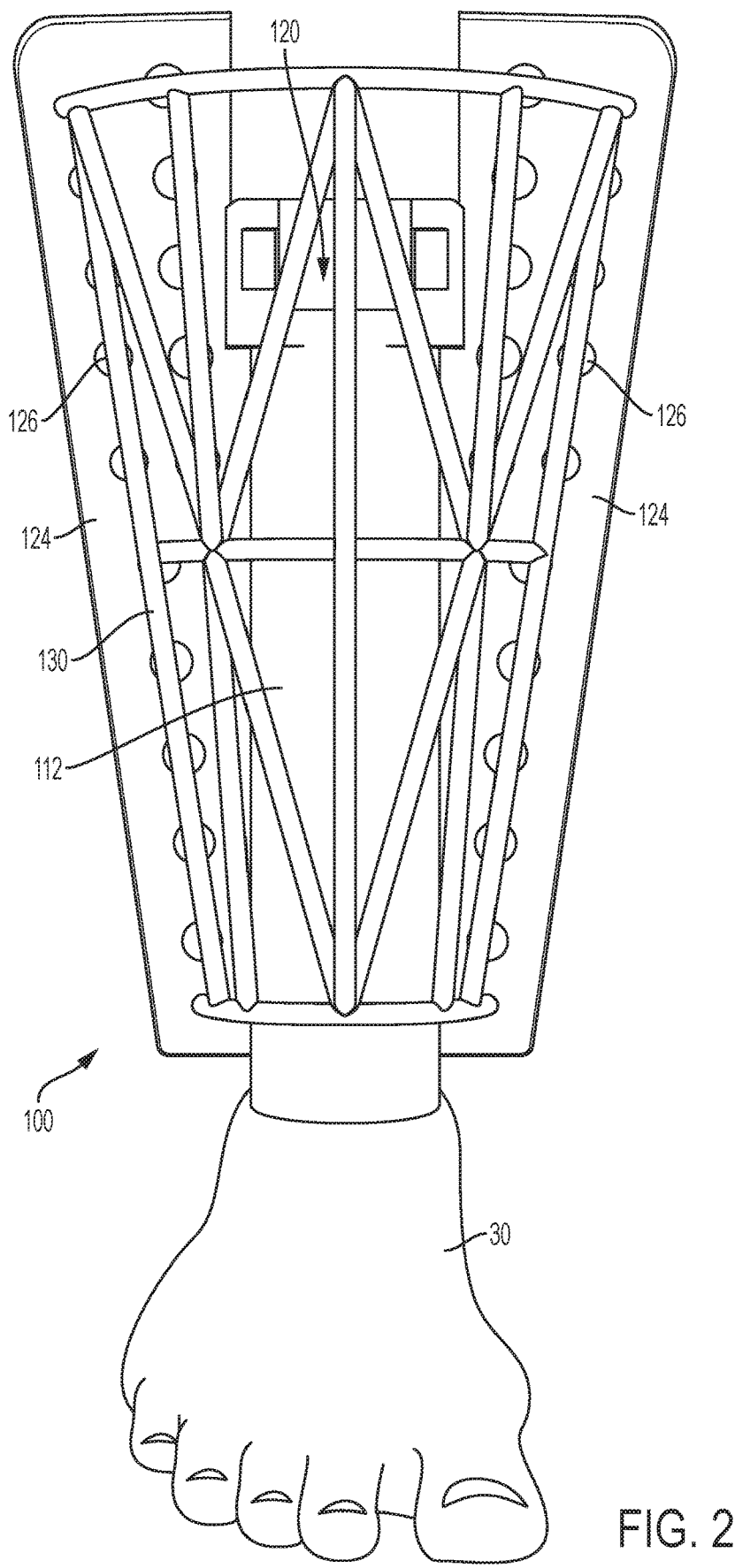
FIG. 2 is a perspective view of a prosthesis according to another exemplary embodiment of the present invention.

FIG. 2 shows a transtibial prosthesis, generally designated by reference number 100, according to another exemplary embodiment of the present invention. The prosthesis 100 has the same general structure as that of the prosthesis 10, including a pylon 112, water attachment 120, fins 124 and holes 126. However, in this embodiment, the prosthesis 100 further includes an outer shell 130 that generally surrounds the other components of the prosthesis 100 for protection and to provide for better fit to the wearer's clothing. Also, as shown in FIG. 2, the holes 126 may be arranged in adjacent columns along the length of the fins 124.

The fins of the water attachment may be made by 3D printing so that fins can be easily formed to match the needs of the patient and then attached to the prosthesis. In the case in which the prosthesis includes permanently affixed fins, the entire prosthesis may be formed by 3D printing with appropriate modifications to the fins. The prosthesis and fins may be made of, for example, nylon and/or carbon fiber.

Although described in the context of a transtibial (or below-the-knee) prosthesis, it should be appreciated that the present invention is also applicable to any other full or partial leg prosthesis.

Having described this invention with regard to specific embodiments, it is to be understood that the description is not meant as a limitation since further modifications and variations may be apparent or may suggest themselves to those skilled in the art. It is intended that the present application cover all such modifications and variations.

The invention claimed is:

1. A prosthesis comprising:
   a socket configured to receive a residual limb;
   a pylon attached to the socket, the pylon comprising a first end portion nearest the socket and a second end portion opposite the socket, the pylon comprising at least one fin that extends downwardly from the first end portion to at least a midpoint between the first end portion and the second end portion; and
   an artificial foot attached to the second end portion of the pylon opposite the socket,
   wherein the prosthesis allows a wearer to perform activities in a land environment, enter a water environment, perform activities in the water environment and then return to the land environment without requiring removal or replacement of the prosthesis.

2. The prosthesis of claim 1, wherein the at least one fin comprises two fin members, each of the fin members tapered inwardly from the first end portion along the length of the pylon.

3. The prosthesis of claim 2, wherein each fin member comprises at least one hole.

4. The prosthesis of claim 3, wherein each fin member comprises a plurality of holes positioned along the length of the fin member.

5. The prosthesis of claim 1, wherein the at least one fin is detachable from the pylon.

6. The prosthesis of claim 1, wherein the at least one fin and the pylon are a unitary structure.

7. The prosthesis of claim 1, wherein the prosthesis is a transtibial prosthesis.

* * * * *